US012702857B2

(12) United States Patent
Cotter et al.

(10) Patent No.: US 12,702,857 B2
(45) Date of Patent: Aug. 11, 2026

(54) APPARATUS FOR PRE-SURGICAL SKIN TREATMENT

(71) Applicant: Wisconsin Alumni Research Foundation, Madison, WI (US)

(72) Inventors: Lisa Cotter, Madison, WI (US); Eric Cotter, Madison, WI (US); Brian Foley Grogan, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 231 days.

(21) Appl. No.: 18/229,780

(22) Filed: Aug. 3, 2023

(65) Prior Publication Data

US 2025/0041621 A1 Feb. 6, 2025

(51) Int. Cl.
*A61N 5/06* (2006.01)

(52) U.S. Cl.
CPC .... *A61N 5/0616* (2013.01); *A61N 2005/0628* (2013.01); *A61N 2005/0632* (2013.01); *A61N 2005/0642* (2013.01); *A61N 2005/0645* (2013.01); *A61N 2005/0652* (2013.01); *A61N 2005/0663* (2013.01)

(58) Field of Classification Search
CPC .......... A61N 5/0616; A61N 2005/0628; A61N 2005/0632; A61N 2005/0642; A61N 2005/0645; A61N 2005/0652; A61N 2005/0663; A61N 5/06–2005/073
See application file for complete search history.

(56) References Cited

U.S. PATENT DOCUMENTS

| | | | | |
|---|---|---|---|---|
| 4,279,254 | A * | 7/1981 | Boschetti | G01J 1/429 607/94 |
| 8,523,925 | B2 * | 9/2013 | Gourgouliatos | A61N 5/0617 607/90 |
| 9,150,433 | B2 * | 10/2015 | Maiden | C02F 1/325 |
| 9,205,278 | B2 * | 12/2015 | Gopalakrishnan | H05B 45/12 |
| 9,399,146 | B2 * | 7/2016 | Jones | A61N 5/062 |
| 10,653,890 | B2 * | 5/2020 | Iguchi | A61N 5/0616 |
| 11,771,617 | B2 * | 10/2023 | Kuhns | A61H 9/0092 601/18 |
| 12,109,430 | B2 * | 10/2024 | Kawarai | A61D 1/00 |
| 2008/0172113 | A1 * | 7/2008 | Gourgouliatos | A61N 5/0617 607/90 |
| 2010/0069898 | A1 * | 3/2010 | O'Neil | A61B 18/203 607/90 |

(Continued)

OTHER PUBLICATIONS

Eric J. Cotter et al.; "Efficacy of combinational therapy using blue light and benzoyl peroxide in reducing Cutibacterium acnes bioburden at the deltopectoral interval: a randomized controlled trial." Journal of Shoulder and Elbow Surgery 30, No. 12 (2021): 2671-2681. US.

*Primary Examiner* — Jonathan T Kuo
(74) *Attorney, Agent, or Firm* — Boyle Fredrickson, S.C.

(57) ABSTRACT

A presurgical skin treatment device uses blue light (415 nm) coupled with a real-time, skin-positioned dose sensor to provide precise dosing within a range of eradicating *C. acnes* while reducing skin irritation. Practical incorporation into surgical procedures is provided by a threshold detection providing an indication that correct dose levels have been obtained and/or in an ambulatory device incorporated into a sterile bandage/shield that can be removed immediately prior to surgery.

7 Claims, 3 Drawing Sheets

(56) References Cited

U.S. PATENT DOCUMENTS

2011/0168642 A1* 7/2011 Maiden .................. C02F 1/325
210/138
2013/0030264 A1* 1/2013 Gopalakrishnan ..... H05B 45/12
250/201.1
2014/0067024 A1* 3/2014 Jones .................. A61N 5/0616
607/90
2014/0135874 A1* 5/2014 Dean .................... A61N 5/0616
607/90
2018/0015298 A1* 1/2018 Iguchi ...................... A61N 5/06
2020/0253813 A1* 8/2020 Kuhns .................. A61N 5/0613
2021/0275826 A1* 9/2021 Kawarai .................. A61D 1/00

* cited by examiner

APPARATUS FOR PRE-SURGICAL SKIN TREATMENT

BACKGROUND OF THE INVENTION

The present invention relates to surgery in regions of the body having a high areal density of sebaceous glands and in particular to an apparatus for pretreating the skin to eradicate *Cutibacterium acnes* in the sebaceous glands prior to surgery.

*Cutibacterium acnes* (*C. acnes*), formerly known as *Propionibacterium acnes*, has been identified as one of the most common pathogens associate with surgical site infection and a likely cause of devastating complication of shoulder surgery, particularly arthroplasty surgery, leading to pain, future surgeries, and significant health care costs. Recent investigation characterizing the shoulder microbiome reported no evidence of *C. acnes* in any subdermal tissues including subcutaneous fat, rotator cuff tendon, joint capsule, and cartilage, suggesting that *C. acnes* is solely a skin flora causing infection only after surgical disruption of skin tissue.

Topical methods of eradicating or reducing the skin burden of *C. acnes* include the use of chlorhexidine swabs and application of topical benzoyl peroxide (BPO). Topical BPO has been shown in several studies to be superior to chlorhexidine in reducing bacterial load using cultures of the epidermis and deep sebaceous glands; however, topical BPO has a number of drawbacks including bleaching of clothing, requirement for serial application leading to poor compliance, a potential for irritant and allergic contact dermatitis, and inconsistency in eradicating *C. acnes*. There is also a concern that topical treatments may not penetrate deep enough to eradicate bacteria colonizing 1 mm beneath the skin surface, where the sebaceous glands reside.

Blue light therapy (BLT), with wavelength 405 nm-470 nanometers (nm), is a Food and Drug Administration (FDA) approved modality that has previously been described in the dermatology literature as a highly effective antimicrobial agent against *C. acnes* in mild to moderate inflammatory acne patients. Nevertheless, a recent study concluded that BLT did not yield a significant bactericidal improvement over BPO. See Cotter E J, Cotter L M, Franczek E B, Godfrey J J, Hetzel S J, Safdar N, Dai T, Arkin L, Grogan B F. Efficacy of combinational therapy using blue light and benzoyl peroxide in reducing *Cutibacterium acnes* bioburden at the deltopectoral interval: a randomized controlled trial, J Shoulder Elbow Surg. 2021 December; 30 (12): 2671-2681, doi: 10.1016/j.jse.2021.08.008, Epub 2021 Aug. 31, PMID: 34478863.

SUMMARY OF THE INVENTION

The present inventors have determined that BLT can be effective at higher doses that are still below the levels that would adversely affect human tissue and, accordingly, that blue light treatment is practical so long as accurate dose control can be achieved within this range. The present invention provides reliable dose control by combining a blue light source with a skin mounted dose monitor. In some embodiments, the invention may provide an ambulatory device that can be used without continuous supervision, reducing presurgical use of hospital resources and cost.

More specifically, in one embodiment, the invention provides an apparatus for pre-surgical skin treatment having an array of LEDs providing 415 nm blue light over an area of at least 50 square centimeters and positionable to treat a patient's skin at a skin area. A light sensor positionable on the skin area is adapted to receive and integrate the blue light to provide a dose measurement and to trigger an output indicating a cumulative dose of over 50 joules per square centimeter.

It is thus a feature of at least one embodiment of the invention to provide a presurgical skin treatment that can confidently provide predetermined skin dose with minimal supervision.

In some embodiments, the apparatus may include an adhesive positioned to attach the light sensor to the skin.

It is thus a feature of at least one embodiment of the invention to provide a light sensor positionable directly on the skin for accurate skin dose measurement.

The light sensor may include a solid-state light sensor and a filter preferentially transmitting 415 nm blue light to the solid-state light sensor.

It is thus a feature of at least one embodiment of the invention to provide a low-cost dose sensor largely resistant to errors from ambient lighting using a standard broadband light sensor.

The apparatus may include a human readable display receiving the output indicating a required dose has been obtained.

It is thus a feature of at least one embodiment of the invention to produce an apparatus that can operate unattended and yet positively indicate that pre-surgical activity has been completed for review by a healthcare professional.

The output may control the array of LEDs to turn the LEDs off when a cumulative dose is reached.

It is thus a feature of at least one embodiment of the invention to minimize excess dose to the patient's skin such as may risk irritation.

In one embodiment, the array of LEDs may be mounted to a flexible substrate communicating with an adhesive for attaching the substrate to conform to the skin.

It is thus a feature one embodiment of the invention to provide for an ambulatory presurgical treatment device that can reduce the amount of hospital time required by the patient, for example, allowing treatment initiation by the patient at home, or in the hospital but without the need for dedicated equipment and hospital space. It is another feature of this embodiment to preserve a sterile field in the treatment area after treatment. It is yet another feature of this embodiment to provide a close coupling between the light source and the skin and to enclose the light source eliminating or reducing the need for protective goggles.

In this embodiment, the light sensor may be attached to the flexible substrate to receive light from at least one LED.

It is thus a feature of at least one embodiment of the invention to provide reliable dose sensing self-contained in an adhesive bandage form factor.

In this embodiment, an onboard battery may be provided mechanically communicating with the adhesive for adhesive attachment with the flexible substrate to the skin.

It is thus a feature of at least one embodiment of the invention to provide a fully integrated treatment bandage for ambulatory use without the need for harnesses or the like.

The apparatus may include an electrical switch communicating with the light sensor to set the integration of dose to zero and to connect the array of LEDs to the battery.

It is thus a feature of at least one embodiment of the invention to permit patient initialization of the apparatus prior to treatment.

The switch may operate to set the integration of dose to zero only during a first operation of the switch and the output may be persistent after the first operation of the switch.

It is thus a feature of at least one embodiment of the invention to allow the healthcare professional to reliably determine that treatment has been properly completed even if it is not directly supervised.

These particular objects and advantages may apply to only some embodiments falling within the claims and thus do not define the scope of the invention.

DETAILED DESCRIPTION OF THE PREFERRED EMBODIMENT

Figure 1:
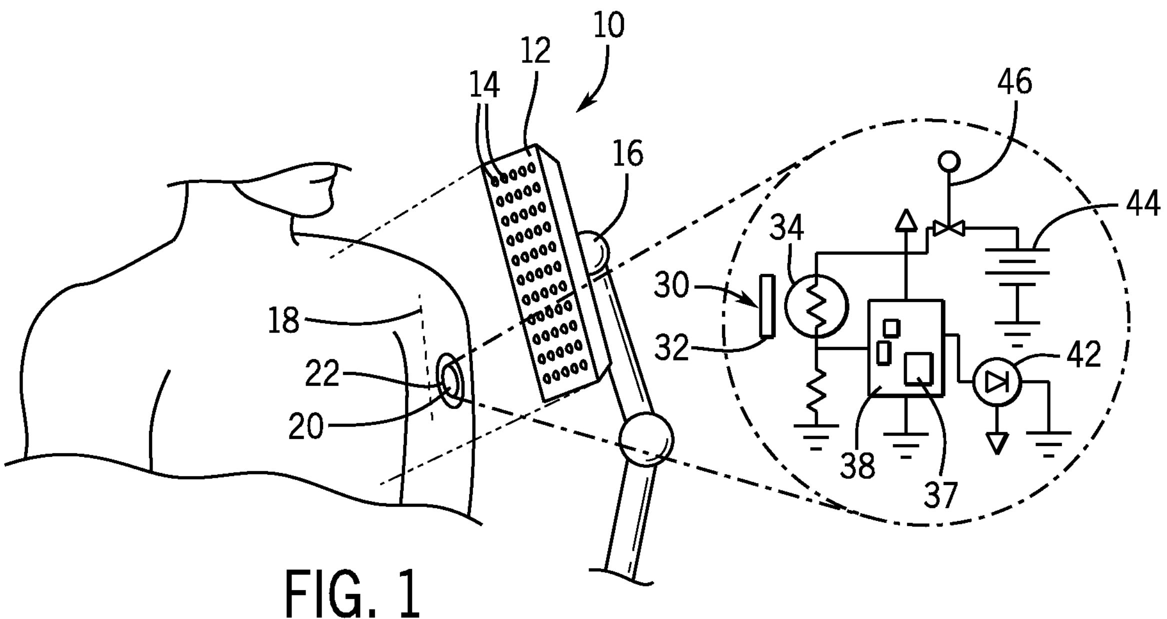
FIG. 1 is a fragmentary elevational view of a patient wearing a skin dose monitor for monitoring blue light treatment and showing the dose monitor schematically in inset.

Referring now to FIG. 1, an apparatus 10 for the treatment of *C. acnes* prior to surgery may provide an LED array 12 having a set of closely spaced LEDs 14 arranged in rows and columns to deliver a substantially uniform field of blue light. The blue light is desirably centered at a frequency of 415 nm plus or minus 5 nm with a bandwidth (FWHM) of 22 nm plus or minus 3 nm plus and provides a flux rate of at least 100 J per square centimeter per hour over an area of at least 50 $cm^2$. An LED array 12 suitable for use with the present invention is commercially available from GlobalMed Technologies of Napa, California, under the trade name Omnilux Blue.

In a first embodiment, the LED array 12 may be mounted on an articulated arm 16 to be positioned facing an area of a surgical incision 18, for example, in the region of a patient shoulder at a distance of approximately 5 cm. Desirably a dose of at least 50 J per square centimeter or at least 75 J per square centimeter will be applied, for example, over a time duration of approximately 31 minutes. The applied dose will be kept to less than an amount that will cause excessive irritation to the patient's skin, for example, less than 100 J per square centimeter.

Figure 2:
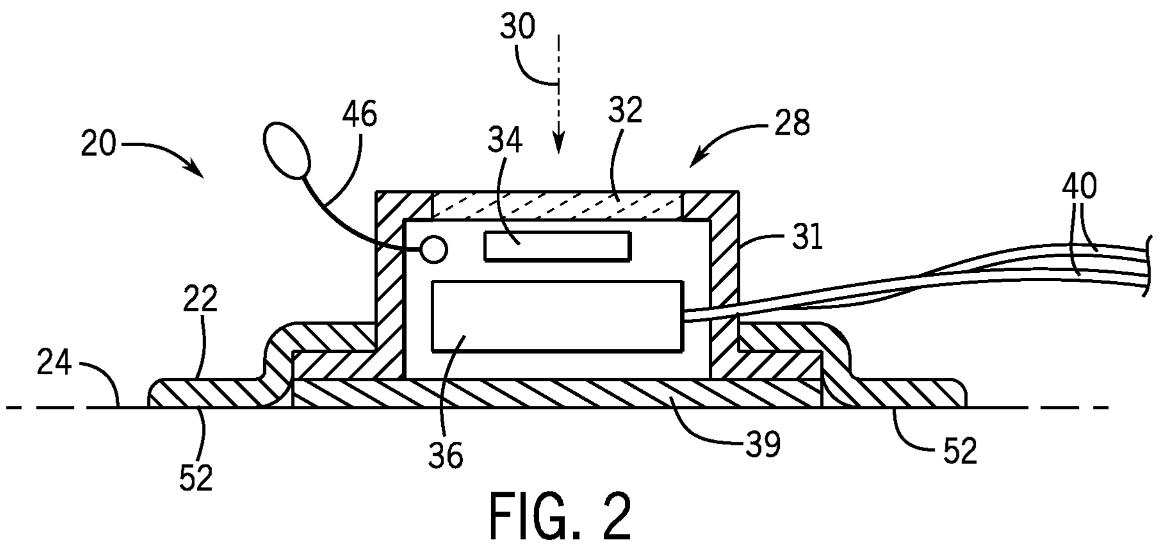
FIG. 2 is an elevational cross-section through the dose monitor of FIG. 1 showing its incorporation into an adhesive bandage.

In order to accurately ensure this range is observed, a skin mounted sensor 20 may be employed, positioned near the area of surgical incision 18 to measure the skin exposure at the skin level. Referring also to FIG. 2, the skin mounted sensor 20 may, in one embodiment, provide a housing 31 with an outwardly extending flange captured by an inner periphery of a surrounding flexible adhesive annulus 22. The adhesive annulus 22 may thus serve to affix the housing 31 to the skin 24, positioning a window 28 of the housing 31 upwardly to receive blue light 30 therethrough. It will be appreciated that other methods of attaching the sensor to the skin, for example, using clastic straps, may also be used. Positioned within the housing 31 beneath the window 28 is a broadband light sensor 34 such as a photo resistor or photodiode that may measure a flux rate of the blue light 30. A narrow bandpass blue light filter 32 is positioned above broadband light sensor 34 to reduce the effect of ambient light on the measurement.

A voltage from the light sensor 34 may be read by a microcontroller 38, for example, the latter having an onboard 10 bit A/D converter for receiving this voltage as well as a processor and volatile and nonvolatile memory. The memory may hold an integration value to be discussed below and an operating program 37.

Using the microcontroller 38, the flux rate of blue light measured by the light sensor 34 is integrated over time to yield a total dose which may be applied against a minimum threshold of 50 or 75 J per square centimeter by internal programming of the microcontroller 38. Upon reaching this threshold an output signal may be generated, for example, through leads 40 connected to the LED array 12 to extinguish the light from the LED array 12. Alternatively or in addition, the output signal may control an interface output 42, for example, an onboard LED signaling that an output has been received. For example the LED may be normally off and may be eliminated when the dose is received or blink at a predetermined rate and duty cycle. As will be discussed below, excess dose may be indicated, for example, by a change in color from green to red. Other outputs, including an audio output or a near field communication with the patient's phone or the like, are also contemplated.

The skin mounted sensor 20 may include an onboard battery 44 providing power to the microcontroller 38 and the light sensor 34 and be activated by a pull tab 46 that may be removed upon use by the patient and which causes a setting to zero of the integration performed by the microcontroller 38. A circuit package 36 including the microcontroller 38, battery 44, output 42, and pull tab 46 may be positioned beneath the light sensor 34 within a housing 31 and separated from the patient's skin 24 by a cushioning gauze layer 39.

The skin mounted sensor 20 not only ensures accurate measurement of the dosed to within the narrow window required by the present invention but can also ensure completion of the treatment particularly if it is not directly supervised by a healthcare professional prior to surgery.

Figures 3, 4, 5:
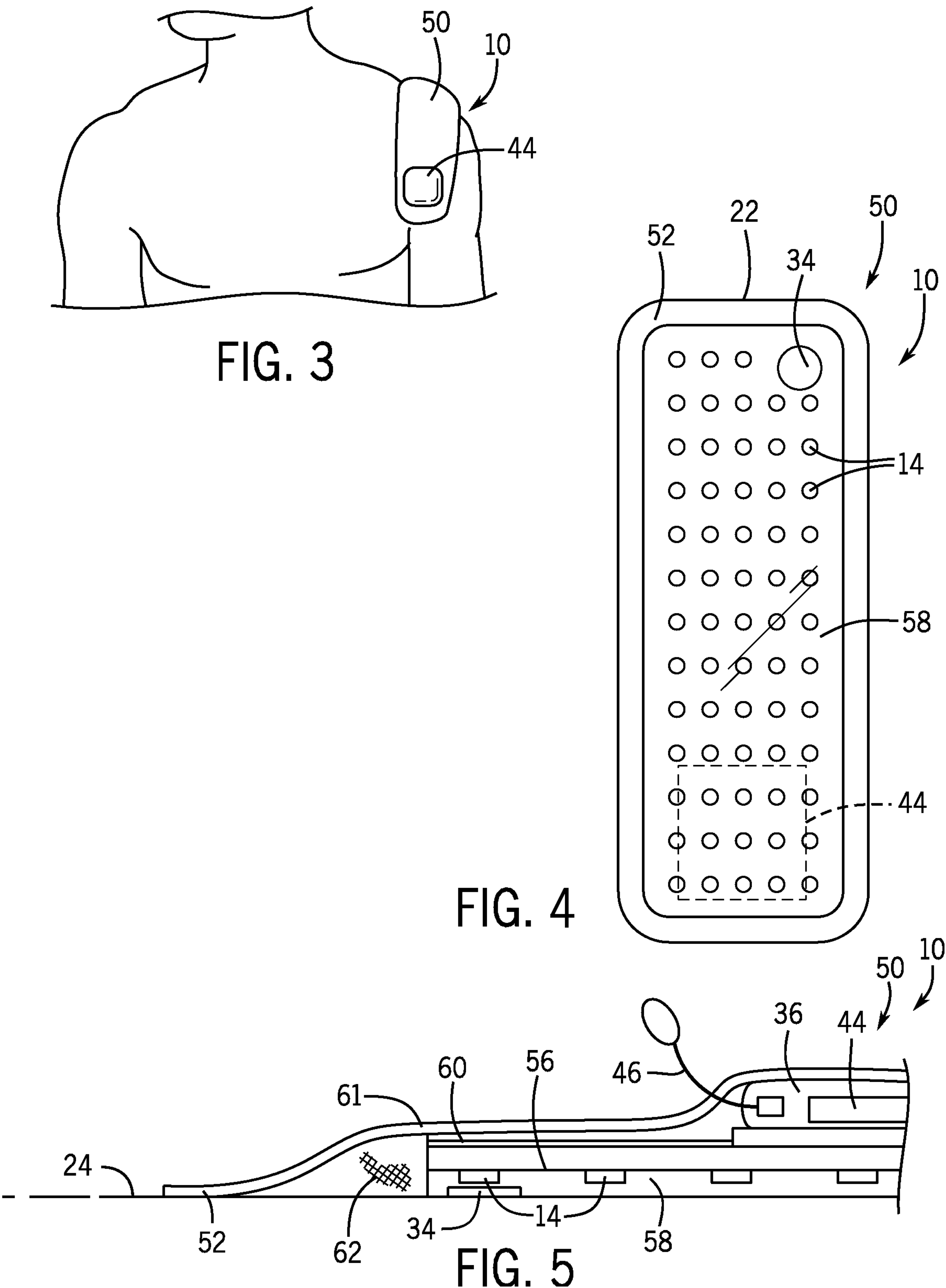
FIG. 3 is an alternative ambulatory implementation of the invention showing an adhesively mounted LED flexible panel in a bandage form factor.
FIG. 4 is a bottom plan view of the panel of FIG. 3 showing the LED array.
FIG. 5 is a figure similar to FIG. 2 showing a cross-section of the panel of FIG. 4.

Referring now to FIGS. 3 and 4, treatment may be facilitated by a second embodiment providing an bandage 50 that may cover the area of surgical incision 18 and attach to the skin with a peripheral adhesive 52. Here the LEDs 14 are mounted to a flexible printed circuit substrate 56 that may conform generally to the patient's skin to lie in close proximity thereto separated by a light diffuser layer 58 and backed by reflective foil layer 60 for maximum efficiency and uniformity. A flexible membrane 61 to which the adhesive 52 is attached may extend inwardly from the periphery over a cushioning transition layer 62 to cover and retain the foil layer 60 and flexible substrate 56 against the skin and to cover and retain an electronics package 36 positioned above the foil layer. The electronics package 36 may include a lightweight lithium polymer battery 44, providing power to the entire system including the LEDs 14 for the duration of treatment while giving the patient full mobility. Here the sensor 34 may be mounted directly beneath a peripheral LED to monitor light output therefrom and to provide the necessary dose rate integration yielding a dose output similar to that described above. More specifically, the dose output may automatically shut off LEDs 14 and provide a signal to the patient or healthcare provider that proper compliance has been obtained. In this version, the sterility of the area of surgical incision 18 is ensured by the covering membrane 61 which may be retained in place until immediately prior to surgery. Other features of this device will be similar to that described with respect to FIGS. 1 and 2.

It will be appreciated that the adhesive attaching the flexible substrate 56 to the skin may be replaced by other attachment mechanisms, for example, elastic straps or the like. To facilitate the use of this embodiment by the patient, in some embodiments, removal of the bandage 50 from the skin may be detected to deactivate the light, for example, using a skin contacting switch, a tear strip breaking a conductor when the bandage 50 is removed, a light sensor detecting ambient light, a capacitive sensor detecting the skin proximity, or the like.

Figure 6:
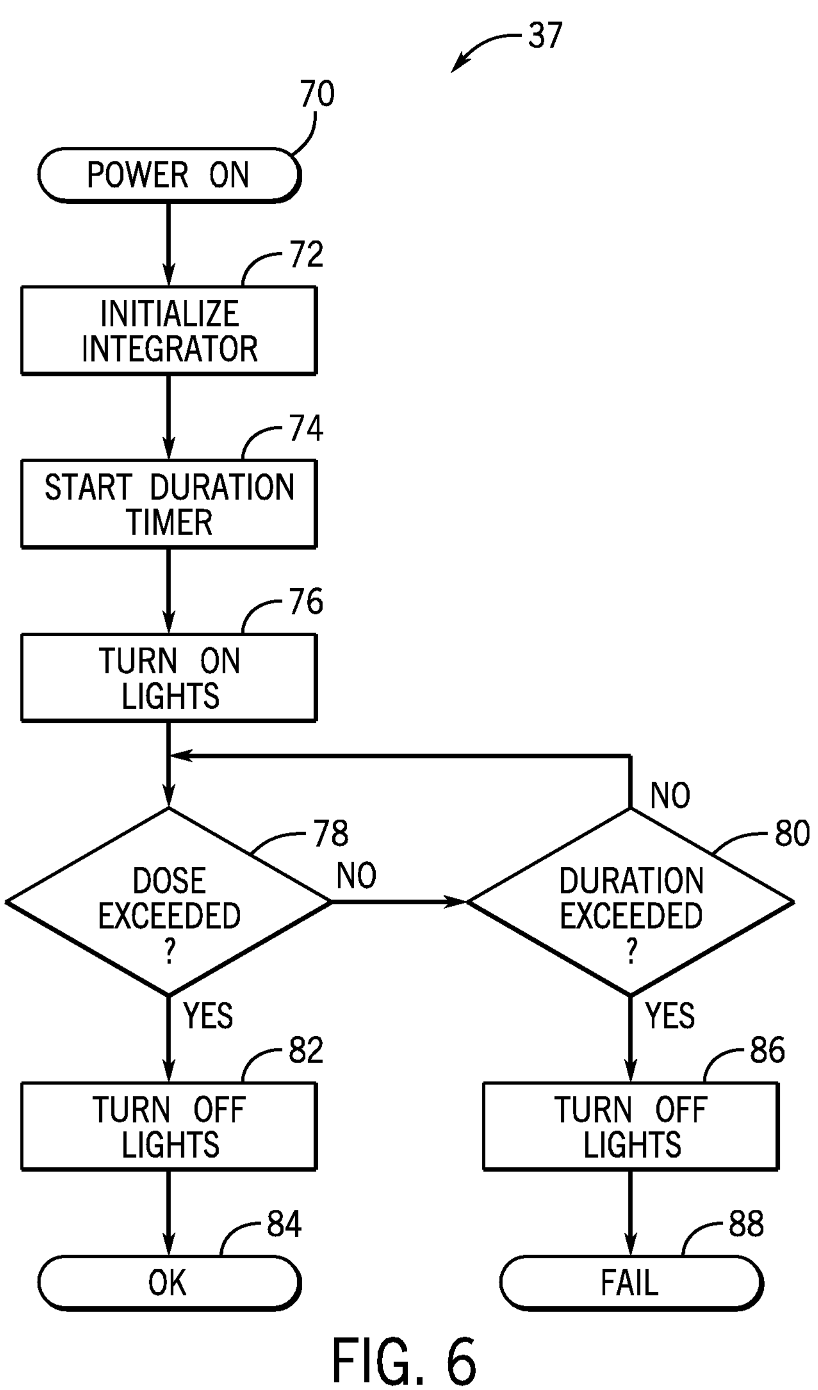
FIG. 6 is a flowchart of a program operation of the device of FIG. 3.

Referring now to FIG. 6, during operation, the pull tab 46 may be removed to activate an internal switch (for example, the pull tab 46 operating to separate inwardly biased spring switch contacts) connecting power to the device. This switching mechanism operates irreversibly to inhibit the ability of the user deactivating the device once activated and to preserve the output state for subsequent review. Upon receiving power, the program 37, as indicated by process block 72, may zero an internal accumulator operating as an integrator of dose having an increasing stored value with successive sampling and accumulation of the voltage from the sensor 34 to provide an ongoing measurement of received energy. At process block 74, a total treatment time timer is started such as will provide an outer bound of the length of treatment. This treatment time timer both ensures uninterrupted treatment and provides safety against sensor failure. A second level of safety is provided by sizing the battery to limit the total amount of energy available for dosing.

At process block 76 power is applied to the LEDs 14 either by the program or by direct connection via the switch communicating with the pull tab 46, and total dose in the integrator is monitored at decision block 78. As long as the dose is below a desired threshold amount (greater than 50 J per square centimeter and in some options greater than 75 J per square centimeter) at process block 80, the duration timer is checked to make sure that a predetermined maximum treatment time has not been exceeded. While the dose values and time values have not been exceeded, the program loops between decision blocks 78 and 80 until, for example, at decision block 78 the dose threshold is achieved. In this case, at process block 82, the LED lights are turned off and at subsequent process block 84, a successful treatment output is created, for example, by illuminating an LED output 42 in a blinking fashion to be persistent with the remaining battery charge for more than 48 hours.

Alternatively, if prior to the dose threshold being reached as determined by decision block 78, the maximum treatment time (for example 25% more than an expected treatment time) is exceeded as determined at decision block 80, the LEDs 14 are turned off at process block 86 and a fail indication is produced at process block 88, most simply being no illumination of the LED 14 or more positively a different color of illumination, for example, a red color instead of the green color, or a different flashing pattern that positively indicates a failure of the dose treatment.

It will be appreciated that the present invention is not limited to use on the shoulder but may be useful in any area of the patient having a large number of sebaceous glands, for example, including not only the shoulders but the back and upper chest. The term dose as used herein refers to a measure of cumulative received areal light energy including but not limited to the units of joules per square centimeter. In all cases where a battery is described, it will be understood that an external power source may be used instead, for example, connected to line power and having medical grade circuit protection. In addition, batteries mounted on the device may also be mounted separately and communicate with the device via conductive leads.

Certain terminology is used herein for purposes of reference only, and thus is not intended to be limiting. For example, terms such as "upper", "lower", "above", and "below" refer to directions in the drawings to which reference is made. Terms such as "front", "back", "rear", "bottom" and "side", describe the orientation of portions of the component within a consistent but arbitrary frame of reference which is made clear by reference to the text and the associated drawings describing the component under discussion. Such terminology may include the words specifically mentioned above, derivatives thereof, and words of similar import. Similarly, the terms "first", "second" and other such numerical terms referring to structures do not imply a sequence or order unless clearly indicated by the context.

When introducing elements or features of the present disclosure and the exemplary embodiments, the articles "a", "an", "the" and "said" are intended to mean that there are one or more of such elements or features. The terms "comprising", "including" and "having" are intended to be inclusive and mean that there may be additional elements or features other than those specifically noted. It is further to be understood that the method steps, processes, and operations described herein are not to be construed as necessarily requiring their performance in the particular order discussed or illustrated, unless specifically identified as an order of performance. It is also to be understood that additional or alternative steps may be employed.

References to "a microprocessor" and "a processor" or "the microprocessor" and "the processor," can be understood to include one or more microprocessors that can communicate in a stand-alone and/or a distributed environment(s), and can thus be configured to communicate via wired or wireless communications with other processors, where such one or more processors can be configured to operate on one or more processor-controlled devices that can be similar or different devices. Furthermore, references to memory, unless otherwise specified, can include one or more processor-readable and accessible memory elements and/or components that can be internal to the processor-controlled device, external to the processor-controlled device, and can be accessed via a wired or wireless network.

It is specifically intended that the present invention not be limited to the embodiments and illustrations contained herein and the claims should be understood to include modified forms of those embodiments including portions of the embodiments and combinations of elements of different embodiments as come within the scope of the following claims. All of the publications described herein, including patents and non-patent publications, are hereby incorporated herein by reference in their entireties.

To aid the Patent Office and any readers of any patent issued on this application in interpreting the claims appended hereto, applicants wish to note that they do not intend any of the appended claims or claim elements to invoke 35 U.S.C. 112 (f) unless the words "means for" or "step for" are explicitly used in the particular claim.

What we claim is:

1. An apparatus for pre-surgical skin treatment comprising:

an array of LEDs providing 415 nm blue light over an area of at least 50 square centimeters and positionable to treat a patient's skin at a skin area;

a light sensor positionable adjacent to the skin of the skin area to receive and integrate 415 nm of blue light received by the skin from the array of LEDs to provide a dose measurement of received light and provide an output indicating when a required dose of at least 50 joules per square centimeter has been received at a desired treatment time;

a timer for measuring elapsed time and having a predetermined maximum time limit greater than the desired treatment time;

an electrical switching circuit communicating with a single activation operator operable only once to connect the array of LEDs to the power, wherein the switching circuit responds to the single activation operator to set an integration of dose and the timer to zero only once, and wherein the electrical switching circuit operates to disconnect the array of LEDs from the power in both cases when either: the output indicates the required dose has been exceeded or the timer has reached the predetermined time limit;

wherein the output is adapted to remain unchanged after the switching circuit disconnects the array of LEDs; and further including a human readable display receiving the output and indicating the required dose has been obtained.

2. The apparatus of claim 1 further including an adhesive positioned to attach the light sensor to the skin.

3. The apparatus of claim 1 wherein the light sensor includes a solid-state light sensor and a filter preferentially transmitting 415 nm blue light to the solid-state light sensor.

4. The apparatus of claim 1 wherein the light sensor provides an output at a time when the dose first exceeds 70 joules per square centimeter.

5. The apparatus of claim 1 wherein the array of LEDs is mounted to a flexible substrate communicating with an adhesive for attaching the substrate to conform to the skin.

6. The apparatus of claim 5 wherein the light sensor is attached to the flexible substrate to receive light from at least one LED of the array of LEDs.

7. The apparatus of claim 6 further including a battery communicating with the adhesive for adhesive attachment with the flexible substrate to the skin.

* * * * *